US006918889B1

(12) United States Patent
Brunel

(10) Patent No.: US 6,918,889 B1
(45) Date of Patent: Jul. 19, 2005

(54) DISPOSABLE INJECTION DEVICE

(75) Inventor: Marc Brunel, Toulouse (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/009,264

(22) PCT Filed: May 25, 2000

(86) PCT No.: PCT/FR00/01420

§ 371 (c)(1),
(2), (4) Date: Dec. 10, 2001

(87) PCT Pub. No.: WO00/76565

PCT Pub. Date: Dec. 21, 2000

(30) Foreign Application Priority Data

Jun. 10, 1999 (FR) ............................................ 99 07334

(51) Int. Cl.[7] ............................ A61M 5/00; A61M 5/32
(52) U.S. Cl. ....................................... 604/110; 604/198
(58) Field of Search ................................ 604/187, 197, 604/198, 207, 263, 264, 272, 110, 195, 192

(56) References Cited

U.S. PATENT DOCUMENTS

| 3,046,985 | A | | 7/1962 | Saenz | |
|---|---|---|---|---|---|
| 4,747,835 | A | * | 5/1988 | Sandhaus | 604/192 |
| 4,767,413 | A | | 8/1988 | Haber et al. | |
| 4,863,434 | A | * | 9/1989 | Bayless | 604/198 |
| 5,188,614 | A | | 2/1993 | Hart | |

FOREIGN PATENT DOCUMENTS

| EP | 0 307 367 B1 | 3/1989 |
|---|---|---|
| EP | 0 446 511 A1 | 9/1991 |
| EP | 0 966 983 A1 | 12/1999 |
| FR | 2 733 687 | 11/1996 |
| FR | 2 741 268 | 5/1997 |
| WO | WO 91/13643 | 9/1991 |
| WO | WO 92/17229 | 10/1992 |
| WO | WO 93/00949 | 1/1993 |
| WO | WO 93/23098 | 11/1993 |
| WO | WO 93/25254 | 11/1993 |
| WO | WO 99/37345 | 7/1999 |

* cited by examiner

Primary Examiner—Nicholas D. Lucchesi
Assistant Examiner—Matthew DeSanto
(74) Attorney, Agent, or Firm—Young & Thompson

(57) ABSTRACT

A single-use injection device, includes a pre-filled syringe (1), a syringe body (5) which is integral with the said syringe, and a protective case (10), the syringe body and protective case being provided with elements (9, 14, 15, 21) for relative locking in translation, which permit their relative displacement between a position of injection and a position of protection after use. The injection device includes a locking ring (23), which is provided with digital support elements (24), and locking units (25), which can lock the syringe body (5) and the protective case (10), in their position of injection, during injection, and can be displaced axially, such as to permit relative displacement of the syringe body and protective case, towards their position of protection after use, under the effect of the action of resilient member (27), only when the plunger (4) has reached its end of travel.

22 Claims, 4 Drawing Sheets

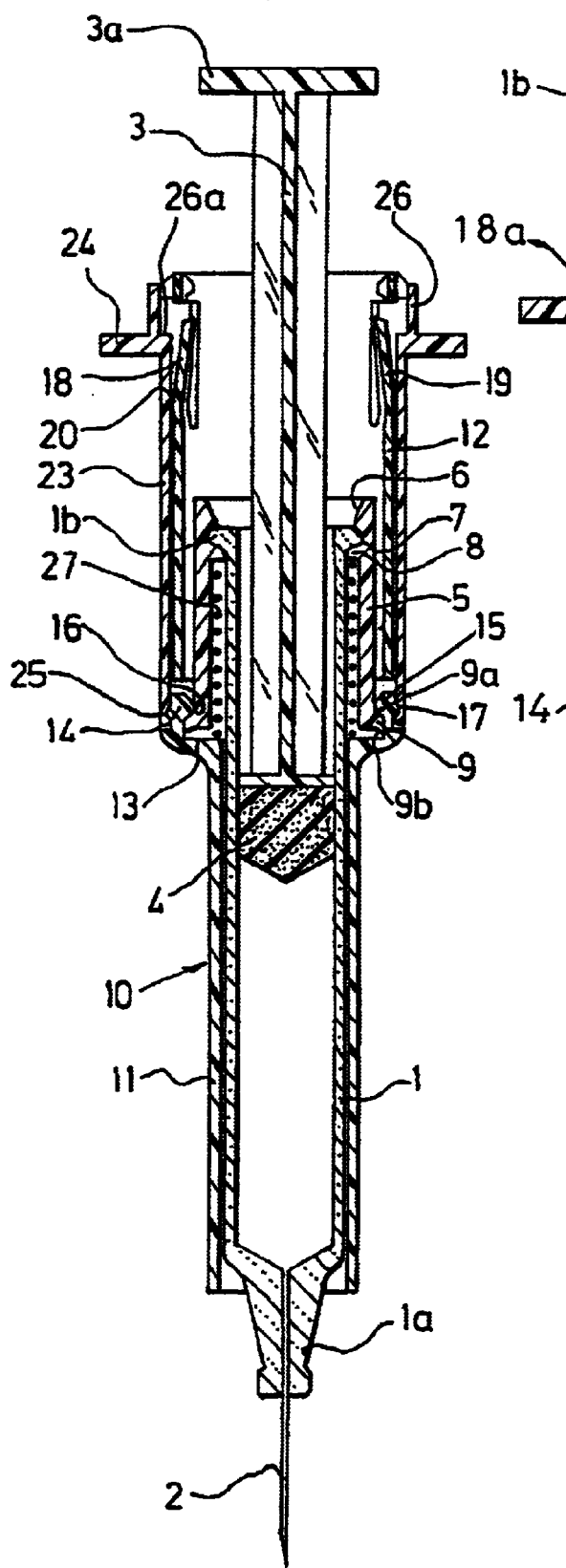
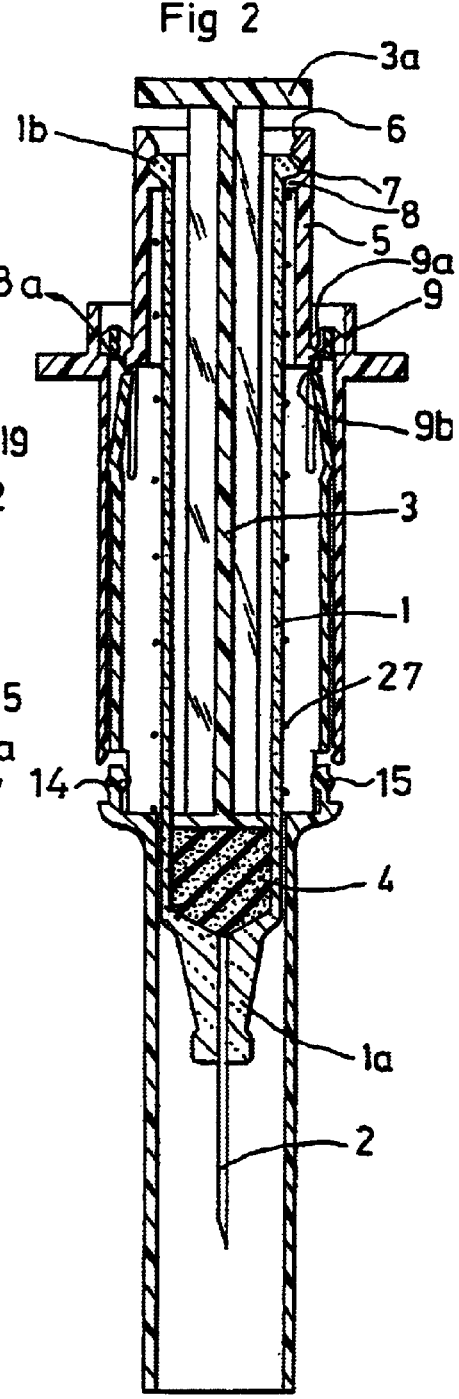

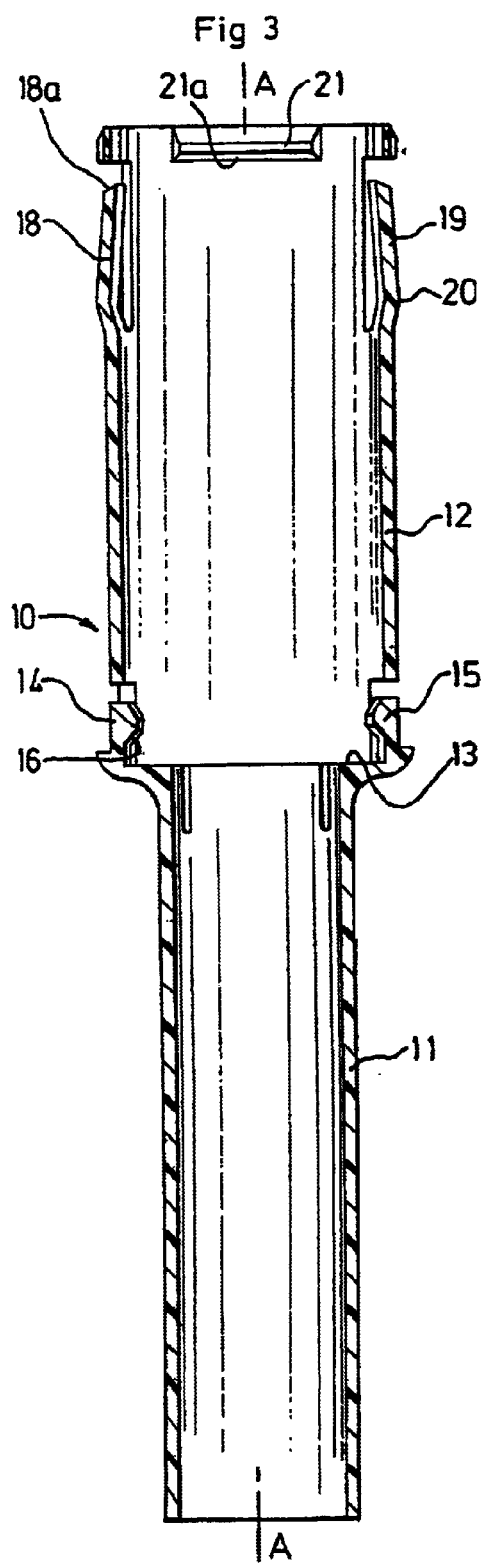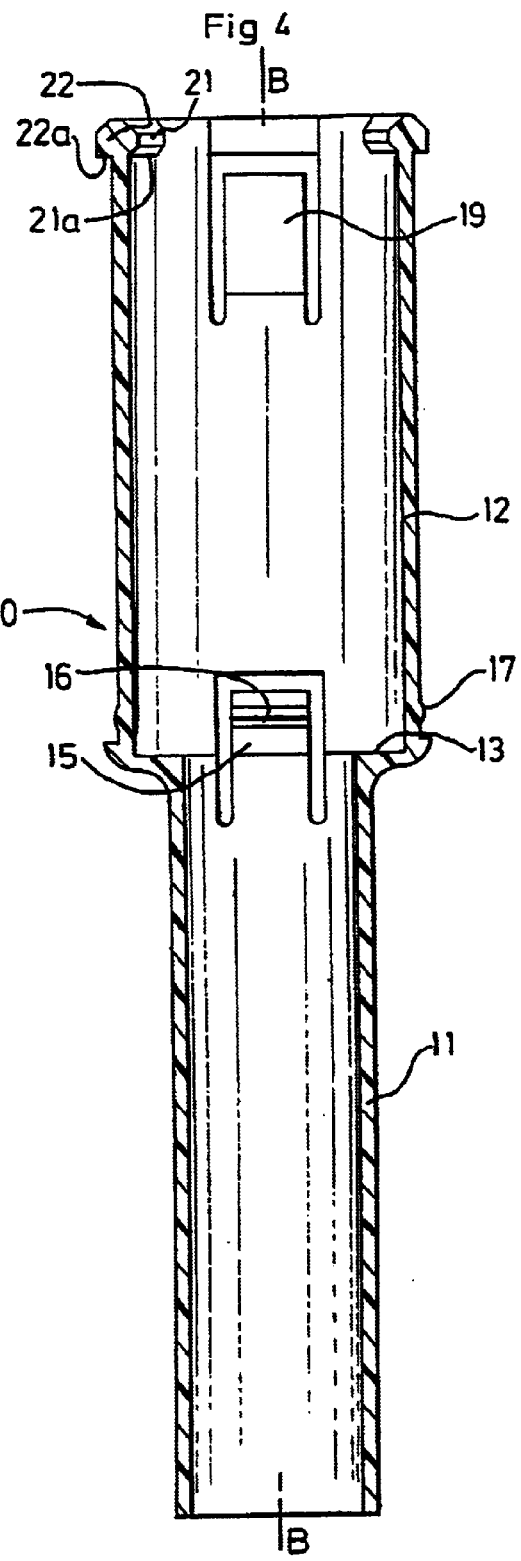

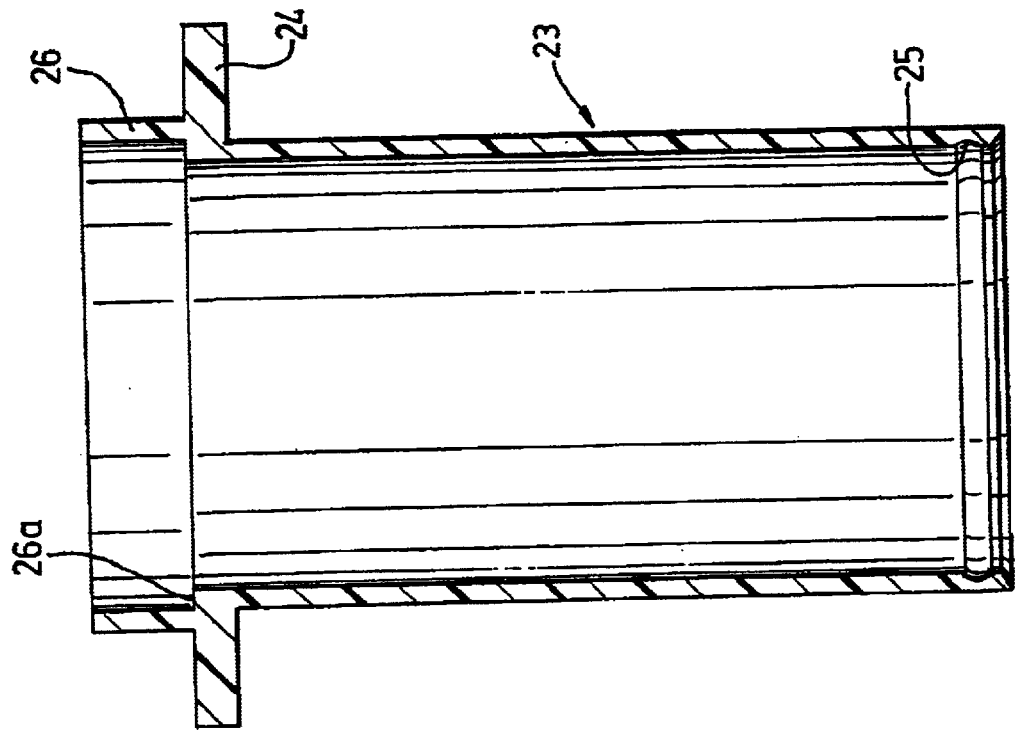
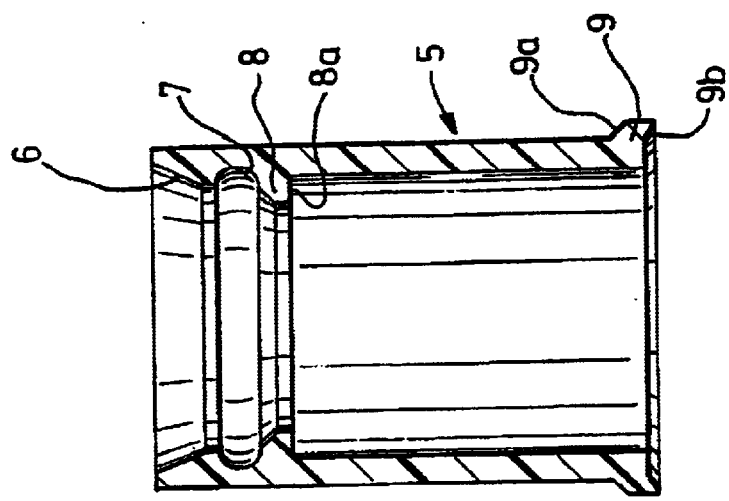

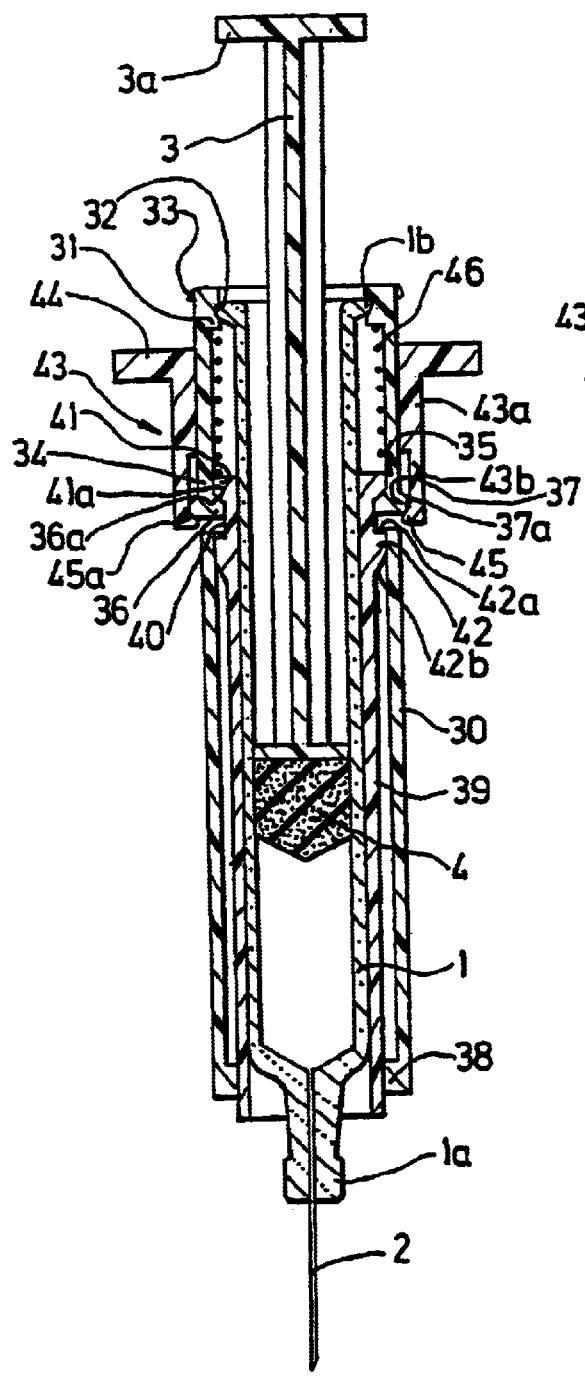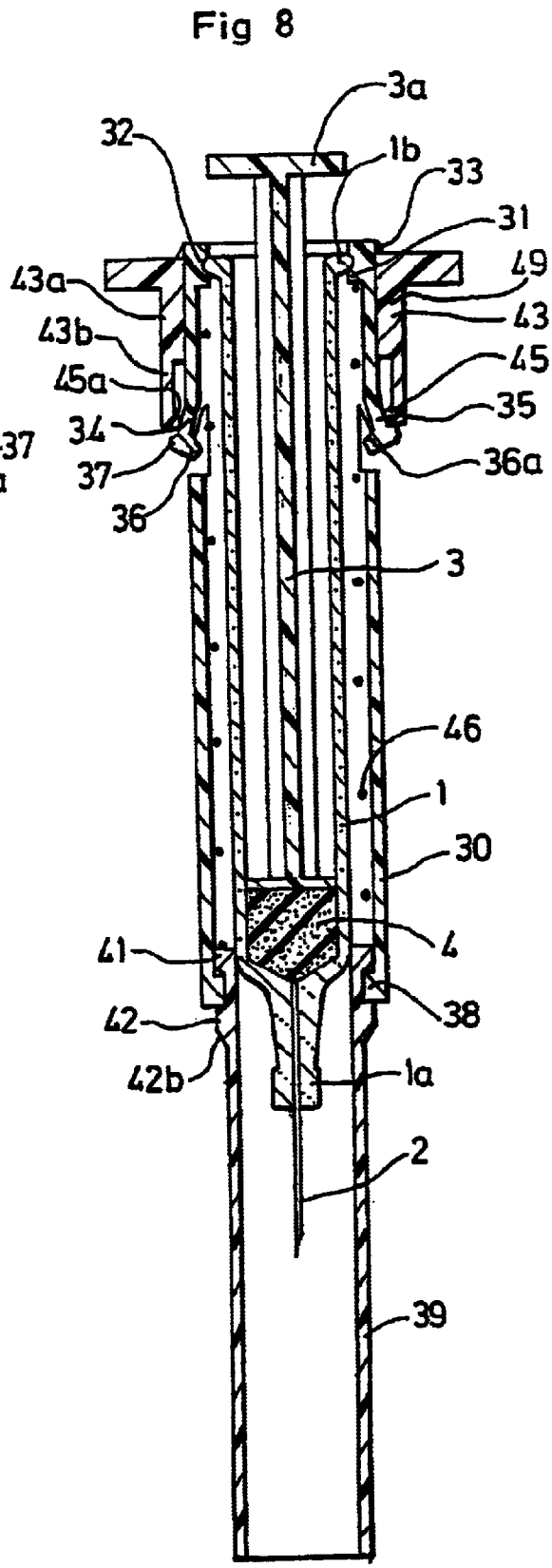
Fig 7
Fig 8

DISPOSABLE INJECTION DEVICE

BACKGROUND OF THE INVENTION

The invention relates to a single-use injection device, which is designed to be pre-filled with a dose of fluid to be injected.

DESCRIPTION OF THE RELATED ART

The single-use injection devices which are conventionally used at present consist of pre-filled syringes which are provided with a cap, which is designed to protect the needle before use, then is removed for the purpose of the injection, and is finally put back into place after the injection has been carried out, in order to prevent subsequent risks of being pricked by the contaminated needle.

However, it has been found that a design of this type has a major disadvantage, derived from the fact that, when the cap is replaced on the needle, the cap must be presented opposite the end of this needle. In fact, this requirement has proved to be the cause of relatively frequent accidents, by being pricked, with all the risks which this pricking with a contaminated needle involves. In addition, syringes of this type have no safety device which is designed to prevent them from being re-used, and particular care must therefore be taken in order to destroy them.

In order to eliminate these disadvantages, the conventional technique consists of providing the injection devices with a protective case, which can slide along the syringe body, or inside which the syringe can be retracted, such as to obtain a position of injection, in which the injection needle is released, or a position of protection after use, in which this injection needle is accommodated and protected inside the protective case.

Furthermore, according to this design, four different general principles are proposed at present, in order to give rise to the sliding of the protective case or of the syringe after use.

According to a first solution, means for relative locking in translation are provided on the syringe body and inside the protective case, such as to make it possible to make the said case slide manually between its positions of injection and of protection after use. According to this solution, this sliding is obtained by holding syringe body with one hand, and displacing the protective case in the direction of the injection needle, with the other hand.

This first solution leads to the production of injection devices with a simple design, such as those described in patent FR 2,733,687, which involve an additional production cost on an industrial scale which is relatively low in comparison with the production cost of a conventional pre-filled syringe without protection. On the other hand, injection devices of this type do not provide absolute safety for their user in relation to the risk of being pricked. In fact, in order to make the protective case slide, after the injection has taken place, the user must apply manual traction on this case, and thus place his fingers on the case, at a relatively short distance from the injection needle. Consequently, and more particularly in the case of injection devices with small dimensions which are designed for injection of small doses of fluid, any sliding of the fingers on the protective case can lead the user to prick himself with the injection needle.

According to a second solution, the injection device comprises resilient means, which are interposed between the syringe body and the protective case, and are designed to be kept compressed and to assure positioning of the protective case and of the syringe in their position of injection, before and during injection, as well as to relax and give rise automatically to sliding of the said protective case or of the said syringe, towards their position of protection after use, on completion of the injection.

This second solution makes it possible to produce injection devices such as those described in international patent applications WO 91.13643, WO 93.23098, WO 93.25254 and European patent EP 446,511 and EP 307,367, which protect against any risk of accidental pricking before and after injection, owing in particular to the fact that the protective case or the syringe are made to slide automatically, owing to triggering of the resilient means, after the injection has taken place.

However, injection devices of this type have a major disadvantage derived from the fact that, during triggering of the resilient means, which is controlled by unlocking means which are disposed on the plunger rod, it is in no way guaranteed that the syringe has been completely emptied, owing to the tolerances accepted concerning the length of syringes during manufacture of the latter. Since injection devices of this type are designed in particular to be used for injection of very small doses of fluids (of approximately a cubic millimeter), the quantity administered of which must be rigorously respected, this technical solution is unsuitable for fulfilling the requirements which apply.

A third solution, which is described in particular in patent U.S. Pat. No. 3,046,985, consists of providing the injection device with independent triggering means, which can be activated by action which is separate from that which gives rise to injection of the fluid. It has been found however, that injection devices of this type, which require specific action other than the natural gesture used for the injection, have been badly received by medical personnel and by patients who administer their own medication, and in fact are very little used.

Finally, the fourth solution, which is described in particular in patents U.S. Pat. No. 4,767,413 and WO 92/17229, consists of providing the injection device with manual locking units, which can make it possible to maintain the protective case in its position of injection by means of pressure by the fingers, and to permit displacement of the case towards its position of protection after use, by releasing the manual pressure exerted. However, this solution has also encountered a negative response from medical personnel and the patients, and is not highly valued at present.

SUMMARY OF THE INVENTION

The object of the present invention is to eliminate all the above-described disadvantages of the techniques for protection after use of the injection devices, and its main objective is to provide an injection device which leads to the fluid being administered in accordance with a natural gesture, and which guarantees total injection of the dose of fluid.

Another objective of the invention is to provide an injection device which cannot be re-used after usage.

For this purpose, the invention relates to a single-use injection device comprising:
  a syringe, comprising an injection needle, and delimiting a chamber filled with a dose of fluid to be injected, which is sealed by a plunger which is integral with one of the ends of a plunger rod, which is provided with a thruster at its opposite end;
  a syringe body which is integral with the syringe;

a protective case;

means for relative locking in translation, provided on the syringe body and the protective case, in order to permit relative displacement of the said protective case and of the syringe/syringe body assembly, between a position of injection, in which the injection needle is released, and a position of protection after use, in which the said injection needle is accommodated inside the protective case.

According to the invention, this injection device is characterised in that it comprises:

resilient means, which are disposed between the syringe body and the protective case, such as to be compressed in the position of injection of the latter; and a locking ring, which is provided with digital support means for injection of the fluid, and units for locking the means for locking in translation of the protective case and of the syringe/syringe body assembly, in the position of injection of the latter, the said locking ring being designed to extend in a position of locking of the said locking means, in the absence of force exerted on the digital support means, and for a force exerted on the latter, which is equivalent to the reaction force generated, thus leading to sliding of the plunger, and is designed to be displaced axially, towards a position in which it releases the said locking means, and permits relative displacement of the protective case and of the syringe/syringe body assembly, towards the position of protection, after use of the latter, by means of the action of resilient means, for a force exerted on the digital support means, which is greater than the reaction force which is generated during sliding of the plunger, and is obtained when the said plunger has reached its end of travel.

The injection device according to the invention thus has the original feature that it comprises a mobile locking ring, which supports the digital support means, and is designed to:

keep the protective case and the syringe/syringe body assembly locked in their position of injection, before injection and during injection, owing to the fact that the force exerted on the thruster of the plunger rod, and the reaction force which is applied to the digital support means, simply gives rise to the sliding of the plunger inside the syringe, and thus the injection of the fluid;

be displaced axially and thus release the means for locking in translation of the protective case and of the syringe/syringe body assembly, only when the plunger has reached the end of travel, i.e. when the said plunger abuts in the syringe, the reaction force is applied entirely on the digital support means, and is then sufficient to displace the locking ring.

Thus, triggering of the protection is obtained by means of the natural gesture which leads to injection of the fluid, and only when the plunger has reached its end of travel, thus guaranteeing administration of all of the dose of fluid.

According to a first advantageous embodiment, the resilient means are disposed between the syringe body and the protective case, such as to generate withdrawal of the syringe/syringe body assembly inside the said protective case, after axial displacement of the locking ring.

According to this embodiment the syringe/syringe body assembly is retracted inside the protective case, firstly after axial displacement of the locking ring, and secondly when the user ceases to exert pressure on the thruster of the plunger rod. Consequently, the triggering takes place gently, without any jolting for the patient.

Also, according to this embodiment, the syringe body advantageously comprises a tubular ring, which is accommodated inside the protective case, the said ring and protective case comprising inner shoulders, between which the resilient means extend. In addition, the locking ring is then fitted around the protective case, such as to be able to slide axially relative to the latter.

The triggering mechanism is thus concealed from the sight of the user, and is not liable to give rise to aversion in the case of a patient who must administer his own dose of medication.

Additionally, and advantageously, the means for relative locking in translation of the tubular ring and of the protective case are disposed such that, in the position of protection after use, the tubular ring extends at least partially in the rear extension of the said protective case.

In this case, the annular ring advantageously has additionally at least one outer surface with a colour different from that of the locking ring and of the protective case. Thus, the identification of an injection device used is immediate.

In addition and advantageously, the protective case comprises at least one tab which can be deformed radially, which supports an element for relative locking in translation of the said protective case in its position of injection, the locking ring being designed to clamp each of the said tabs in its locking position, and to release each tab, such as to permit radial expansion of the latter, during its axial displacement.

In addition and advantageously, the means for relative locking in translation of the tubular ring and of the protective case, in the position of injection of the latter, comprise for each tab an inner boss, which is provided on the latter, and an outer rib, which is provided on the tubular ring, the said boss and rib having conjugated inclined support surfaces.

Furthermore, the means for relative locking in translation of the tubular ring and of the protective case, in the position of protection after use of the latter, advantageously comprise an inner rib, which is provided towards the rear end of the said protective case, and has an inclined support surface which is conjugated with that of the aforementioned outer rib of the tubular ring.

In addition, the protective case advantageously comprises at least one tab which can be deformed radially, which is provided spaced from the rear rib of the said protective case, and is designed to assure the locking in translation of the outer rib of the tubular ring, each of the said tabs having a natural, radially expanded position, which can permit initial fitting of the tubular ring, and is designed to be retracted radially, such as to project inside the protective case, during fitting of the locking ring.

Tabs of this type are designed firstly in order to permit fitting of the tubular ring, by means of their production in a radially expanded position, then to project inside the protective case, after the locking ring has been put into place, such as to constitute non-return elements, which prevent the injection device from being re-used.

Advantageously, the locking ring also comprises a rear tubular section, which is designed to surround the rear inner rib of the protective case, such as to shrink the latter on, and to prevent any risk of escape of the tubular ring.

Advantageously, this locking ring also comprises an inner shoulder, which is provided at the level of its rear tubular section, the protective case comprising a boss to stop the said shoulder, after the said locking ring has been displaced axially.

The protective case advantageously comprises a rear section with a diameter which is designed to accommodate the tubular ring, and along which the locking ring extends, and a front section, with a diameter which is conjugated with the outer diameter of the syringe, the said rear and front sections being separated by an inner shoulder for support of the resilient means.

In order to render the annular ring integral on the syringe, this syringe advantageously comprises a rear collar, the tubular ring comprising a rear inner annular groove, with a cross-section which is designed to accommodate the said collar.

The protective case advantageously additionally comprises an outer annular rib, the means for locking the locking ring consisting of an inner annular groove which is provided in the said locking ring, and has a cross-section which is designed to accommodate the said outer rib.

According to a second advantageous embodiment, the resilient means are disposed between the syringe body and the protective case, such as to give rise to sliding of the said protective case along the syringe, after axial displacement of the locking ring.

By continuing to exert pressure on the thruster of the plunger rod, once the plunger has reached its end of travel, the triggering obtained in this case results in making the protective case slide along the syringe/syringe body assembly, as far as a position in which the protective needle is accommodated in the said protective case.

Additionally, according to this embodiment, the syringe body advantageously comprises a tubular sheath, inside which the protective case is accommodated, the resilient means extending in the said tubular case, in the rear extension of the said protective case. Additionally, the locking ring is then fitted around the tubular sheath, such as to be able to slide axially relative to the latter.

Additionally, and advantageously, the tubular sheath comprises at least one tab which can be deformed radially, which supports an element for relative locking in translation of the said sheath in its position of injection, the locking ring being designed to clamp each of the said tabs in its locking position, and to release each tab, such as to permit radial expansion of the latter, during its axial displacement.

In addition, advantageously, the means for relative locking in translation of the tubular sheath and of the protective case, in the position of injection of the latter, comprise for each tab an inner boss which is provided on the latter, and an outer rib, which is provided on the protective case, the said boss and rib having conjugated inclined support surfaces.

In addition, the means for relative locking in translation of the tubular sheath and of the protective case, in the position of protection after use of the latter, advantageously comprise a second outer rib, which is provided on the protective case, and delimits a groove together with the first outer rib, and an inner rib, which is provided at the level of the front end of the tubular sheath, and has a shape which is designed to be accommodated in the groove.

The tubular sheath advantageously comprises an outer rib, which is provided on the said sheath at the level of each tab, the means for locking the locking ring consisting of an inner annular groove, which is delimited by a front rib, which is designed to abut beneath the rib of the tubular sheath.

This tubular sheath also advantageously comprises a rear outer annular rib, to stop the locking ring after axial displacement of the latter.

Finally, in order to ensure that the tubular sheath is rendered integral on the syringe, this syringe advantageously comprises a rear collar, the tubular sheath comprising a rear inner annular groove, with a cross-section which is designed to accommodate the said collar.

DESCRIPTION OF THE DRAWINGS

Other characteristics, objects and advantages of the invention will become apparent from the following detailed description, provided with reference to the attached drawings which represent two preferred embodiments, by way of non-limiting example. In these drawings:

FIG. 1 is a longitudinal cross-section through an axial plane, of a first embodiment of an injection device according to the invention, in the position of injection of the latter;

FIG. 2 is a longitudinal cross-section through an axial plane, in the position of protection after use of this injection device;

FIG. 3 is a longitudinal cross-section through an axial plane B of the protective case of this injection device;

FIG. 4 is a longitudinal cross-section through an axial plane A of this protective case;

FIG. 5 is a longitudinal cross-section through an axial plane of the tubular ring of this injection device;

FIG. 6 is a longitudinal cross-section through an axial plane of the locking ring of this injection device;

FIG. 7 is a longitudinal cross-section through an axial plane of a second embodiment of an injection device according to the invention, in the position of injection of the latter; and FIG. 8 is a longitudinal cross-section through an axial plane of this second embodiment, in the position of protection after use of the injection device.

DESCRIPTION OF THE PREFERRED EMBODIMENTS

The injection devices according to the invention, represented respectively in FIGS. 1, 2 and 7, 8, both comprise firstly a pre-filled syringe 1 of a conventional type, which for example is made of glass, comprising in a conventional manner a front nose 1a, on which there is, fitted a needle 2, and a collar 1b at the level of its rear end.

This syringe 1 also comprises in a conventional manner a plunger rod 3, which is provided with a thruster 3a at the level of its rear end, and activates a plunger 4 which is integral with its front end.

The injection device represented in FIGS. 1 and 2 additionally comprises a syringe body, which is designed to be rendered integral with the syringe 1, and consists of a tubular ring 5, which is represented in detail in FIG. 5.

This tubular ring 5 comprises firstly a rear end portion 6 with a frusto-conical shape, forming a ramp which allows it to pass over the collar 1b of the syringe 1, and, juxtaposed with the said frusto-conical portion, an inner groove 7 with a cross-section which is designed to accommodate the said collar, delimited by an inner annular rib 8, which has a radial support surface 8a, opposite the said groove.

At the level of its front end, this tubular ring 5 additionally comprises an outer annular rib 9, with two front surfaces 9a, 9b, which are parallel and inclined relative to the axis of the said tubular ring.

The injection device additionally comprises a protective case 10, which is represented in FIGS. 3 and 4, and is designed to accommodate the tubular ring 5, and inside which the syringe 1 is retracted after use.

This protective case 10 consists of two longitudinal sections 11, 12, which are separated by a radial inner shoulder 13:

a front section 11, with an inner diameter which is conjugated with the outer diameter of the syringe 1; and a rear section 12, with an inner diameter which is substantially greater than the outer diameter of the tubular ring 5, and is designed to accommodate the latter.

The protective case 10 firstly comprises two tabs 14, 15, which are deformable radially, and are disposed in a manner diametrically opposite the vicinity of the front end of the rear section 12, and are each delimited by a cut-out in the shape of an inverted U, provided in the peripheral wall of the said protective case.

Each of these tabs 14, 15 has an inner surface in the general shape of a dihedron, forming an inclined front frontal surface 16, which is designed to constitute a support surface for the rear frontal surface 9b of the rib 9, thus making it possible to lock the tubular ring 5 in translation. Surface 16 serves as an inner boss.

This protective case 10 additionally comprises two non-return tabs 18, 19, which can be deformed radially, are disposed in the rear third of the rear section 12, at a short distance from the end of the latter, each co-axially relative to one of the tabs 14, 15, and delimited by cut-outs in the shape of an inverted U, provided in the peripheral wall of the said protective case.

This protective case 10 additionally comprises two other tabs 18, 19, which can be deformed radially, are disposed in the rear third of the rear section 12, at a short distance from the end of the latter, each co-axially relative to one of the tabs 14, 15, and delimited by cut-outs in the shape of an inverted U, provided in the peripheral wall of the said protective case.

Each of these non-return tabs 18, 19, which are known as non-return tabs, is produced during moulding, in an "open" position, i.e. such that it does not project inside the rear section 12, and thus permits fitting of the tubular ring 5 inside the said rear section.

In order to be able to be retracted, such that the end section 18a of these non-return tabs 18, 19, forms a non-return stop inside the rear section 12, as explained hereinafter, each of these non-return tabs 18, 19 additionally has an outer boss 20, which makes it possible to fold them back during fitting of the locking ring described hereinafter.

At the level of the rear end of the rear section 12, and offset by 90° relative to the non-return tabs 18, 19, the protective case 10 additionally comprises:

two inner ribs serving as inner bosses 21, each of which has an inclined front frontal surface 21a, which is designed to constitute a support surface for the rear frontal surface 9b of the rib 9 of the tubular ring 5; and two outer bosses 22, each of which has a front frontal surface 22a, which abuts radially.

Finally, the injection device comprises a locking ring 23 with an inner diameter and a length conjugated with the outer diameter and the length of the rear section 12 of the protective case 10, which ring is designed firstly to retract the non-return tabs 18, 19 radially, when it is fitted along the said rear section.

Firstly, at the level of its rear end, this locking ring 23 comprises an outer digital support collar 24. At the level of its front end, it also comprises an inner annular groove 25, with a cross-section which is designed to accommodate the boss 17 of the protective case 10.

Finally, this locking ring 23 comprises a cylindrical section 26, which extends in the rear extension of the digital support collar 24, and, together with the latter, delimits an inner radial stop shoulder 26a.

The production of the injection device previously described comprises the following main steps.

Firstly, a spring 27 is accommodated in the tubular ring 5, and the latter is placed in the rear section 12 of the protective case 10, such as to lock the front frontal surface 9a of the rib 9 beneath the front frontal surface 16 of the tabs 14, 15. In this position, the spring 27 is compressed between the inner radial shoulder 13 of the protective case 10, and the radial support surface 8a of the inner rib 8 of the tubular ring 5.

It should also be noted that, as previously stated, the introduction of the tubular ring 5 inside the protective case 10 is permitted by means of the "open" position obtained during moulding of the non-return tabs 18, 19.

The locking ring 23 is then fitted along the rear section 12 of the protective case 10, until the groove 25 accommodates the outer boss 17 of the said protective case, in which position the said locking ring locks the tubular ring 5 in translation, relative to the protective case 10, by supporting the front frontal surface 16 of the tabs 14, 15 on the front frontal surface 9a of the rib 9. It should also be noted that, when the locking ring 23 is put into place, it forces the non-return tabs 18, 19 to retract radially by contact with the boss 20 of the said tabs.

The final operation consists of integrating the pre-filled syringe 1, by introducing the latter into the rear section 12 of the protective case 10, until the collar 1b is locked in the inner groove 7 of the tubular ring 5, in which position the injection needle 2 extends in the front extension of the said protective case. It should be noted that, when the syringe 1 is put into place, the presence of the frusto-conical ramp of rear end portion 6 facilitates introduction of the latter inside the tubular ring 5.

The injection device obtained, represented in FIG. 1, is then used conventionally for the purpose of an injection, by exerting support force on the thruster 3a of the plunger rod, and reaction support force on the digital support collar 24 of the locking ring 23.

During this injection, since the resistance which opposes the displacement of the plunger 4 is naturally lower than the force to be exerted in order to displace the locking ring 23 axially, the latter remains positioned in its position of locking the units 9, 14, 15 for relative locking in translation of the tubular ring 5 and of the protective case 10.

On the other hand, when the plunger 4 has reached its end of travel, i.e. when all of the dose of fluid has been injected, the same support and reaction forces make the locking ring 23 rise axially along the rear section 12 of the protective case 10, until the shoulder 26a of the latter abuts radially the outer bosses 22 of the said protective case.

The tabs 14, 15 of the protective case 10 are then released, and when the user releases the pressure exerted on the thruster 3a of the plunger rod 3, the tubular ring 5/syringe 1 assembly is retracted inside the protective case 10, under the action of the spring 27.

As represented in FIG. 2, and on completion of retraction, the front frontal surface 9a of the rib 9 of the tubular ring 5 abuts the frontal surface 21a of the inner bosses 21 of the protective case 10, in which position the said rib 9 is locked in translation in both directions, between the bosses 21 and the non-return tabs 18, 19 of the said protective case.

It should also be noted that the cylindrical section 26 of the locking ring 23 forms a hoop around the rear portion of the rear section 12 of the protective case 10, in which the bosses 21 are provided, and thus guarantees against any risk of escape of the tubular ring 5, at the end of travel of the latter.

It should also be noted that, since the tubular ring 5 extends in the rear extension of the protective case 10, after use, the latter can advantageously have a colour which is different from that of the other elements, such as to permit immediate identification of the used injection devices.

The injection device previously described is thus provided with an automatically triggered protection system, which is designed to make it possible to administer the fluid to be injected in accordance with a natural gesture, and the triggering of which takes place only when the full dose of fluid has been injected. In addition, this injection device is designed such that it cannot be re-used, unless of course certain locking elements of the said device have been damaged.

In addition to the syringe 1/plunger rod 3/plunger 4 assembly previously described, the injection device represented in FIGS. 7 and 8 comprises firstly, a syringe body tubular sheath 30 consisting of a tubular sheath, with an inner diameter which is greater than the outer diameter of the syringe 1, and is designed to accommodate a protective case described hereinafter, in the annular space delimited by the said syringe body and syringe.

This tubular sheath 30, which has a length substantially shorter than that of the syringe 1, comprises firstly a rear annular inner rib 31, in which there is provided an annular groove 32, for locking the collar 1b of the said syringe.

At the level of its rear end, this tubular sheath 30 also comprises an annular rear outer rib 33. Substantially a quarter of the way along its length from its rear end, this tubular sheath 30 also comprises two diametrically opposed tabs 34, 35, which can be deformed radially, each of which is delimited by a cut-out in the shape of a U, provided in the peripheral wall of the said tubular sheath.

Each of these tabs 34, 35 comprises firstly an inner boss 36, which has an inclined rear frontal surface 36a, and secondly an outer boss 37, which has an inclined front frontal surface 37a. Boss 37 is in the form of a rib.

Finally, at the level of its front end, the tubular sheath 30 comprises an annular lower inner rib 38, which defines two frontal radial stop surfaces.

In addition, the injection device comprises a protective case 39, with an inner diameter which is conjugated with the outer diameter of the syringe, and an outer diameter which is conjugated with the inner diameter of the tubular sheath 30, at the level of the rib 38 of the latter.

Additionally, this protective case 39 has a length which is designed such that its rear end section extends opposite the tabs 34, 35 of the tubular sheath 30, and its front end extends substantially in the front extension of the said tubular sheath.

In order to lock it in translation, in an ejection position in which the needle 2 is released, this protective case 39 comprises an annular outer groove 40, which can accommodate the inner boss 36 of the tabs 34, 35, and is delimited by two outer ribs 41, 42, with outer diameters which are conjugated with the inner diameter of the tubular sheath 30:

a rear outer rib 41, which is provided with an inclined front frontal surface 41a, for support against the rear frontal surface 36a of the boss 36 of the tabs 34, 35; and a front outer rib 42, which is provided with a rear, radial stop frontal surface 42a, and an inclined front frontal surface 42b.

Finally, the injection device comprises a locking ring 43, with an inner diameter which is conjugated with the outer diameter of the tubular sheath 30, and has a length designed to extend approximately three-quarters of the way along the length of the section of the said tubular sheath, which is contained between the front ends of the tabs 34, 35, and the rear end of this tubular sheath 30.

At the level of its rear end, this locking ring 43 comprises firstly an outer digital support collar 44.

It also has a rear tubular section 49, with an inner diameter which is conjugated with the outer diameter of the tubular sheath 30, and a tubular front section 43b with an inner annular groove, with a diameter which is substantially greater than that of the outer diameter of the said tubular sheath, forming a groove delimited by an inner front rib 45, which is provided with an inclined rear frontal surface 45a, for support against the inclined front surface 37a of the bosses 37 of the tabs 34, 35 of the tubular sheath 30. Bosses 37 are in the form of outer ribs.

The production of the injection device previously described comprises the following main steps.

Firstly, a spring 46 is introduced into the syringe body 30, then the protective case 39 is also introduced into this syringe body 30, until the groove 40 accommodates the inner bosses 36 of the tabs 34, 35. In this position, the spring 46 is compressed between the front surface of the rib 31 of the syringe body 30 and the rear end surface of the protective case 39.

The locking ring 43 is then fitted along the syringe body 30, until the inner rib 45 locks the said syringe body in translation relative to the protective case 39, by supporting the rear frontal surface 36a of the rib 36 against the front surface 41a of the rib 41.

The final operation consists of integrating the pre-filled syringe 1, by introducing it into the protective case 39, until the collar 1b is locked in the groove 32 of the syringe body 30.

As in the previous case, the injection device obtained, represented in FIG. 7, is then used conventionally, in accordance with a natural gesture which consists of exerting support pressure on the thruster 3a, and reaction support force on the digital support collar 44 of the locking ring 43.

As in the previous case, these support and reaction force pressures give rise firstly to sliding of the plunger 4, then, when the latter has reached its end of travel, they make the locking ring 43 rise along the syringe body tubular sheath 30, until the ring abuts the rear rib 33 of the said syringe body.

The tabs 34, 35 of the syringe body 30 are then released, such that the protective case 39, which is thrust by the spring 46, is made to slide along the syringe 1, to an advanced position in which the groove 40 of the latter accommodates the lower rib 38 of the syringe body 30.

It should be noted that this position of locking in translation of the protective case 39 in its advanced position can be obtained by inclining the front frontal surface 42b of the rib 42 of this protective case 39, which makes it possible for this rib 42 to pass over the lower rib 38 of the syringe body 30.

On the other hand, when it is in its advanced position, the protective case cannot be retracted, owing to the radial stop 42a formed by the rear frontal surface of the rib 42.

What is claimed is:

1. A single-use injection device comprising:
    a syringe, comprising an injection needle, and delimiting a chamber filled with a dose of fluid to be injected, which is sealed by a plunger which is integral with one of the ends of a plunger rod, which is provided with a thruster at its opposite end;
    a syringe body which is integral with the syringe;
    a protective case;
    means for relative locking in translation, provided on the syringe body and the protective case, in order to permit relative displacement of the protective case and of the syringe and syringe body assembly, between a position of injection, in which the injection needle is released, and a position of protection after use, in which the injection needle is accommodated inside the protective case, wherein the injection device comprises:
    resilient means, which are disposed between the syringe body and the protective case, such as to be compressed in the position of injection of the latter; and
    a locking ring, which is provided with digital support means for injection of the fluid, and units for locking in translation of the ring, which can maintain the ring in a position in which it locks the means for locking in translation of the protective case and of the syringe and syringe body assembly, in the position of injection of the latter, in the absence of force exerted on the digital support means, and for a force exerted on the latter, which is equivalent to the reaction force generated, thus leading to sliding of the plunger, and in order to permit axial displacement of the ring towards a position in which it releases the locking means, and permits relative displacement of the protective case and of the syringe and syringe body assembly, towards the position of protection, after use of the latter, by means of the action of the resilient means, for a force exerted on the digital support means, which is greater than the reaction force which is generated for the purpose of sliding of the plunger, and is obtained when the plunger has reached its end of travel.

2. An injection device as claimed in claim 1, wherein the resilient means are disposed between the syringe body and the protective case, such as to generate withdrawal of the syringe and syringe body assembly inside the protective case, after axial displacement of the locking ring.

3. An injection device as claimed in claim 2, wherein:
the syringe body comprises a tubular ring, which is accommodated inside the protective case, the ring and protective case comprising inner shoulders, between which the resilient means extend; and
the locking ring is fitted around the protective case, such as to be able to slide axially relative to the latter.

4. An injection device as claimed in claim 3, wherein the protective case comprises at least one tab which can be deformed radially, which supports an element for relative locking in translation of the protective case in its position of injection, the locking ring being designed to clamp each of the tabs in its locking position, and to release each tab, such as to permit radial expansion of the latter, during its axial displacement.

5. An injection device as claimed in claim 4, wherein the means for relative locking in translation of the tubular ring and of the protective case, in the position of protection after use of the latter, comprise an inner rib, which is provided towards the rear end of the protective case, and has an inclined support surface which is conjugated with that of the outer rib of the tubular ring.

6. An injection device as claimed in claim 5, wherein the locking ring comprises a rear tubular section, which is designed to surround a rear inner rib of the protective case.

7. An injection device as claimed in claim 6, wherein the locking ring comprises an inner shoulder, which is provided at the level of its rear tubular section, the protective case comprising a boss to stop the inner shoulder of the locking ring, after the locking ring has been displaced axially.

8. An injection device as claimed in claim 5, wherein the protective case comprises at least one tab which can be deformed radially, which is provided spaced from the rear rib of the protective case, and is designed to assure the locking in translation of the outer rib of the tubular ring, each of the tabs having a natural, radially expanded position, which can permit initial fitting of the tubular ring, and is designed to be retracted radially, such as to project inside the protective case, during fitting of the locking ring.

9. An injection device as claimed in claim 4, wherein the means for relative locking in translation of the tubular ring and of the protective case, in the position of injection of the latter, comprise for each tab an inner boss, which is provided on the latter, and an outer rib, which is provided on the tubular ring, the said boss and rib having conjugated inclined support surfaces.

10. An injection device as claimed in claim 3,
wherein the said protective case comprises a read extension, and
wherein the means for relative locking in translation of the tubular ring and of the protective case are disposed such that, in the position of protection after use, the tubular ring extends at least partially in the rear extension of the protective case.

11. An injection device as claimed in claim 10, wherein the annular tubular ring has at least one outer surface with a colour different from that of the locking ring and of the protective case.

12. An injection device as claimed in claim 3, wherein the protective case comprises a rear section with a diameter to accommodate the tubular ring, and along which the locking ring extends, and a front section, with a diameter which is conjugated with an outer diameter of the syringe, the rear and front sections being separated by an inner shoulder for support of the resilient means.

13. An injection device as claimed in claim 3, wherein the syringe comprises a rear collar, the tubular ring comprising a rear inner annular groove, with a cross-section which is designed to accommodate the collar.

14. An injection device as claimed in claim 3, wherein the protective case comprises an outer annular rib, the means for locking the locking ring consisting of an inner annular groove which is provided in the locking ring, and has a cross-section which is designed to accommodate the outer rib.

15. An injection device as claimed in claim 1, wherein the resilient means are disposed between the syringe body and the protective case, such as to give rise to sliding of the protective case along the syringe, after axial displacement of the locking ring.

16. An injection device as claimed in claim 15, wherein:
the protective case comprises a rear extension;
the syringe body comprises a tubular sheath, inside which the protective case is accommodated, the resilient means extending in the tubular sheath, in the rear extension of the protective case; and
the locking ring is fitted around the tubular sheath, such as to be able to slide axially relative to the latter.

17. An injection device as claimed in claim 16, wherein the tubular sheath comprises at least one tab which can be deformed radially, which supports an element for relative locking in translation of the sheath in its position of injection, the locking ring being designed to clamp each of the tabs in its locking position, and to release each tab, such as to permit radial expansion of the latter, during its axial displacement.

18. An injection device as claimed in claim 17, wherein the means for relative locking in translation of the tubular sheath and of the protective case, in the position of injection of the latter, comprise for each tab an inner boss which is provided on the latter, and an outer rib, which is provided on the protective case, the boss and rib having conjugated inclined support surfaces.

19. An injection device as claimed in claim 17, wherein the means for relative locking in translation of the tubular sheath and of the protective case, in the position of protection after use of the latter, comprise a second outer rib, which is provided on the protective case, and delimits a groove together with a first outer rib provided on the protective case, and an inner rib, which is provided at the level of the front end of the tubular sheath, and has a shape which is designed to be accommodated in the groove.

20. An injection device as claimed in claim 17, wherein the tubular sheath comprises an outer rib, which is provided on the sheath at the level of each tab, the means for locking the locking ring consisting of an inner annular groove, which is delimited by a front rib, which is designed to abut beneath a rib of the tubular sheath.

21. An injection device as claimed in claim 16, wherein the tubular sheath comprises a rear outer annular rib, to stop the locking ring after axial displacement of the latter.

22. An injection device as claimed in claim 16, wherein the syringe comprises a rear collar, the tubular sheath comprising a rear inner annular groove, with a cross-section which is designed to accommodate the collar.

* * * * *